(12) United States Patent
Belden

(10) Patent No.: US 7,292,894 B2
(45) Date of Patent: Nov. 6, 2007

(54) METHODS AND APPARATUS FOR JOINING SMALL DIAMETER CONDUCTORS WITHIN MEDICAL ELECTRICAL LEADS

(75) Inventor: Elisabeth L. Belden, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 884 days.

(21) Appl. No.: 10/256,490

(22) Filed: Sep. 27, 2002

(65) Prior Publication Data

US 2004/0064174 A1    Apr. 1, 2004

(51) Int. Cl.
*A61N 1/00* (2006.01)
*H01R 4/10* (2006.01)
(52) U.S. Cl. ........................ 607/122; 439/880
(58) Field of Classification Search ............... 607/122, 607/37–38; 600/394, 373; 439/880, 448
See application file for complete search history.

(56) References Cited

U.S. PATENT DOCUMENTS

| | | | |
|---|---|---|---|
| 4,270,825 A | 6/1981 | Marsh ........................ 339/47 R |
| 4,576,032 A | 3/1986 | Maack et al. .................. 72/431 |
| 4,829,146 A | 5/1989 | Duve | |
| 5,014,720 A * | 5/1991 | Barcel et al. ................ 607/122 |
| 5,246,014 A | 9/1993 | Williams et al. ............. 607/122 |
| 5,531,779 A | 7/1996 | Dahl et al. ................... 607/119 |
| 5,760,341 A | 6/1998 | Laske et al. .............. 174/126.2 |
| 5,882,233 A | 3/1999 | Idehara ........................ 439/877 |
| 5,984,711 A * | 11/1999 | Woodard .................... 439/395 |
| 6,193,743 B1 | 2/2001 | Brayton et al. ................. 607/1 |
| 6,272,273 B1 | 8/2001 | Bookwalter et al. ........ 385/100 |
| 6,310,292 B1 | 10/2001 | Osborn | |
| 2001/0037136 A1 | 11/2001 | Pianca et al. | |

* cited by examiner

*Primary Examiner*—Mark Bockelman
(74) *Attorney, Agent, or Firm*—Paul H. McDowall; Girma Wolde-Michael

(57) ABSTRACT

A conductor assembly and methods for mechanically and electrically coupling a small diameter conductor to a lead component having a relatively larger sized conductor bore is provided. The assembly includes a sizing member sized to fit securely around a relatively small diameter conductor and to further fit within a conductor bore so that temporary compression (e.g., crimping, crushing, or staking) of a discrete portion of the conductor bore mechanically couples, and establishes electrical communication between, the conductor and the lead component. Alternately, a conductive sleeve member having a relatively large diameter conductor bore is adapted to receive a sizing unit to downsize one side of the sleeve member in a manner similar to the foregoing. In this case, a relatively smaller diameter one of a pair of different diameter elongated conductors is firmly mechanically coupled and in electrical communication with a relatively larger diameter conductor.

11 Claims, 7 Drawing Sheets

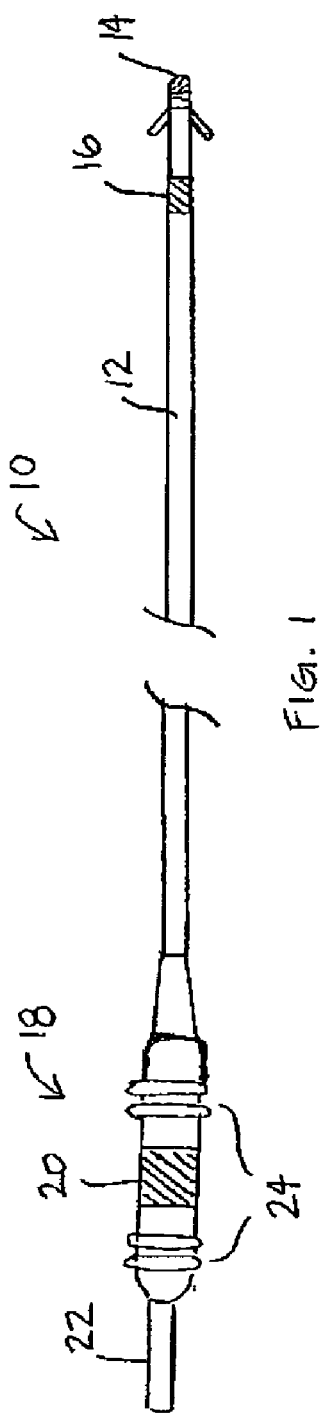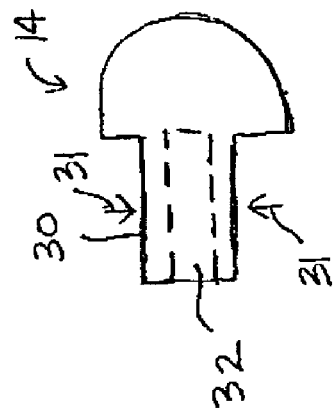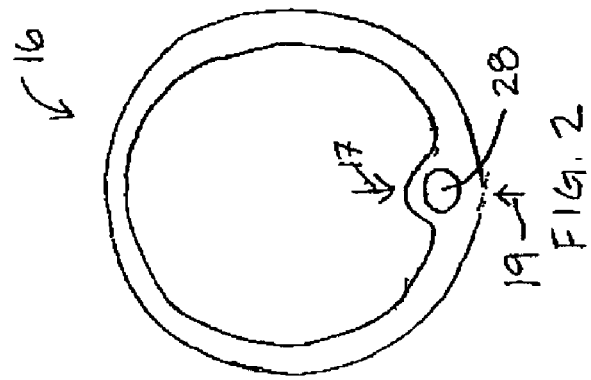

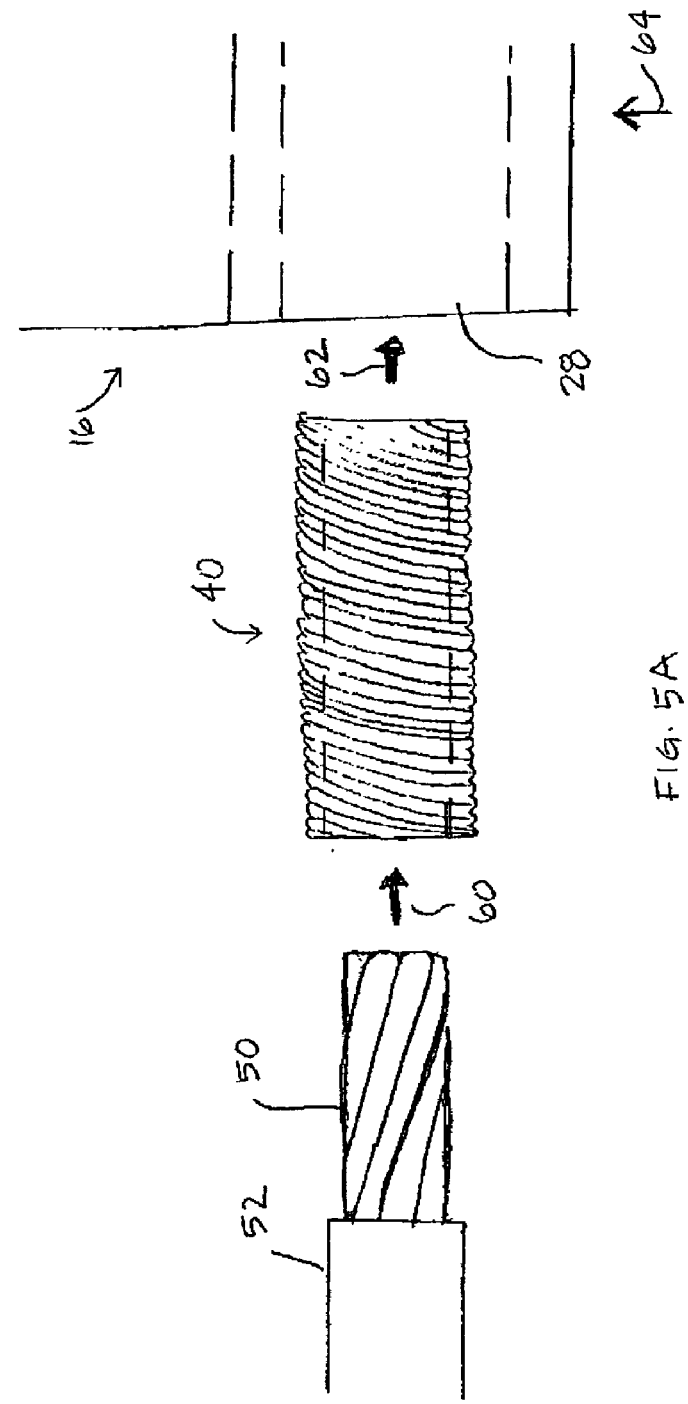

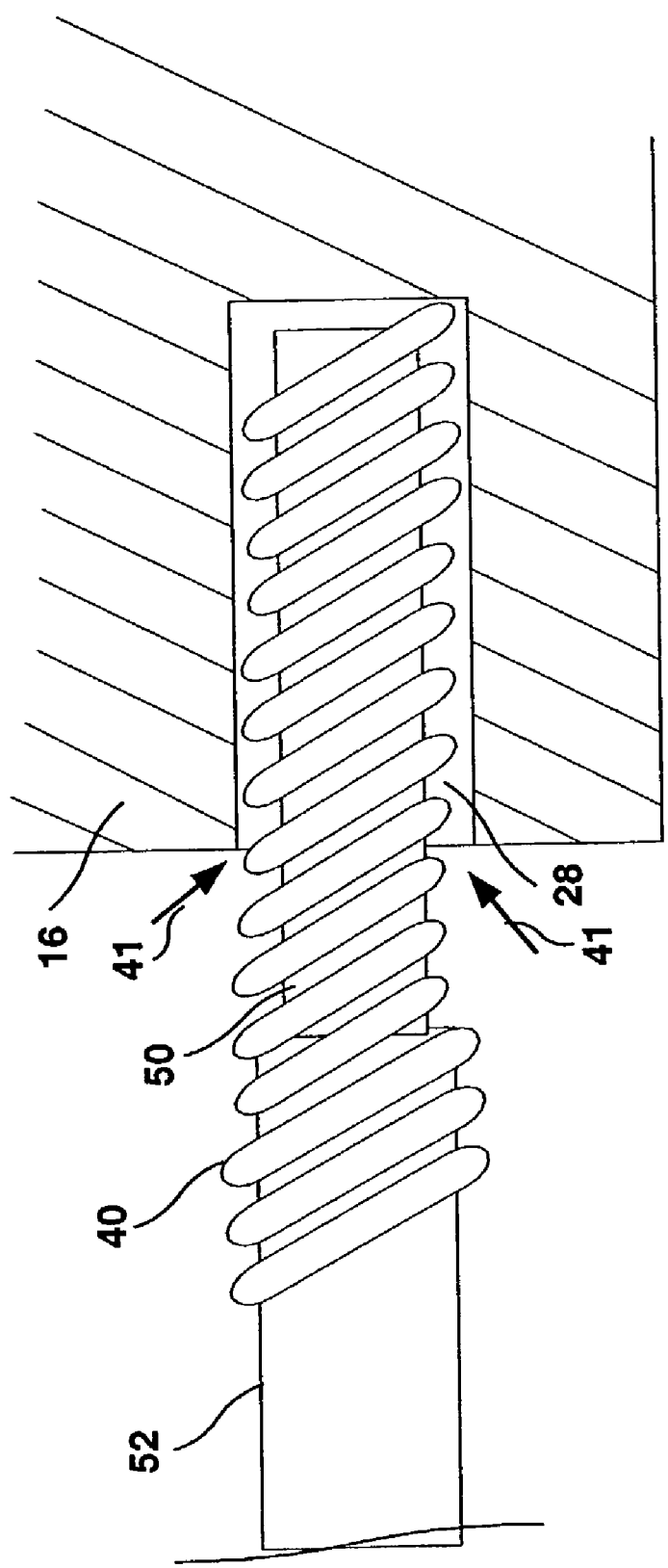

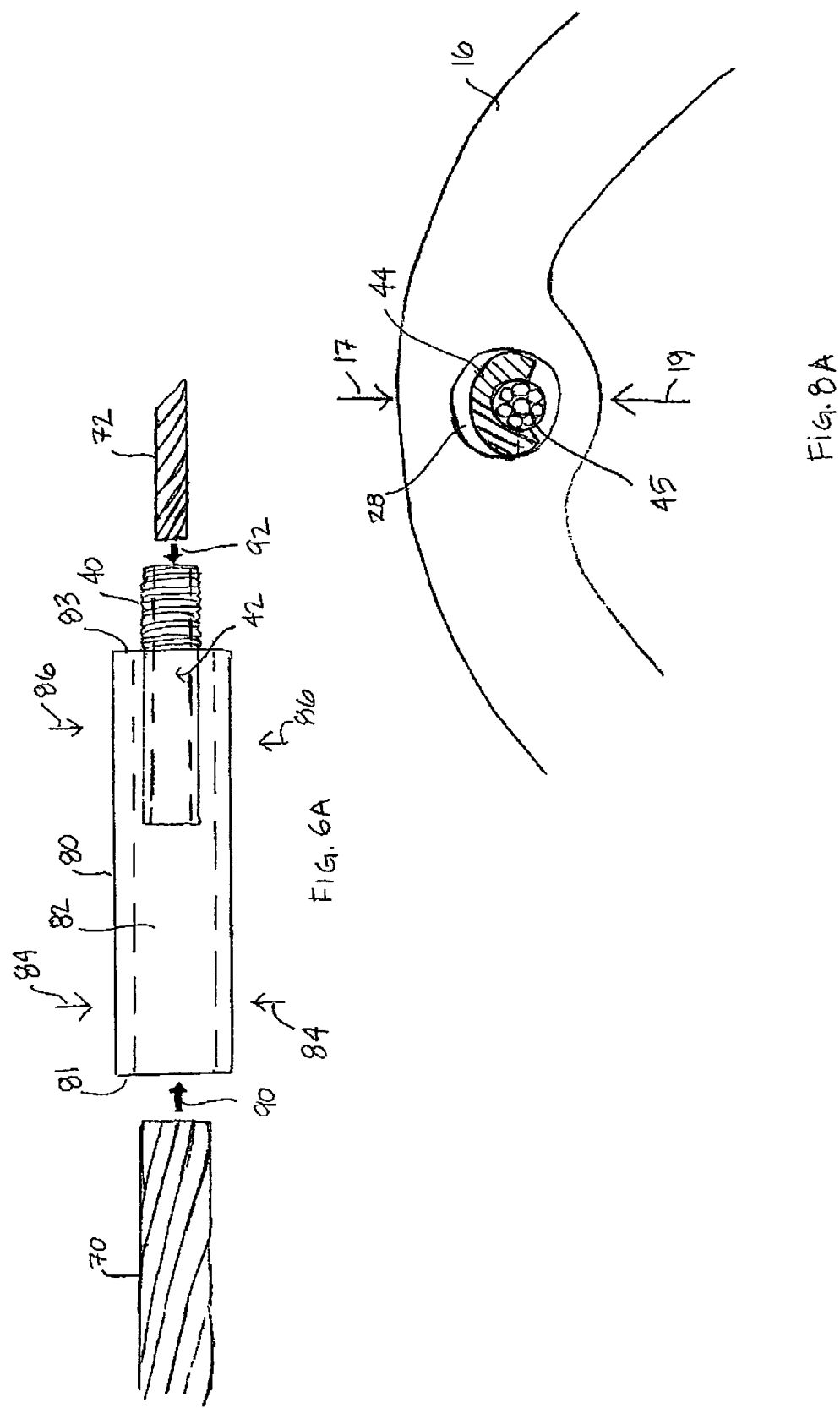

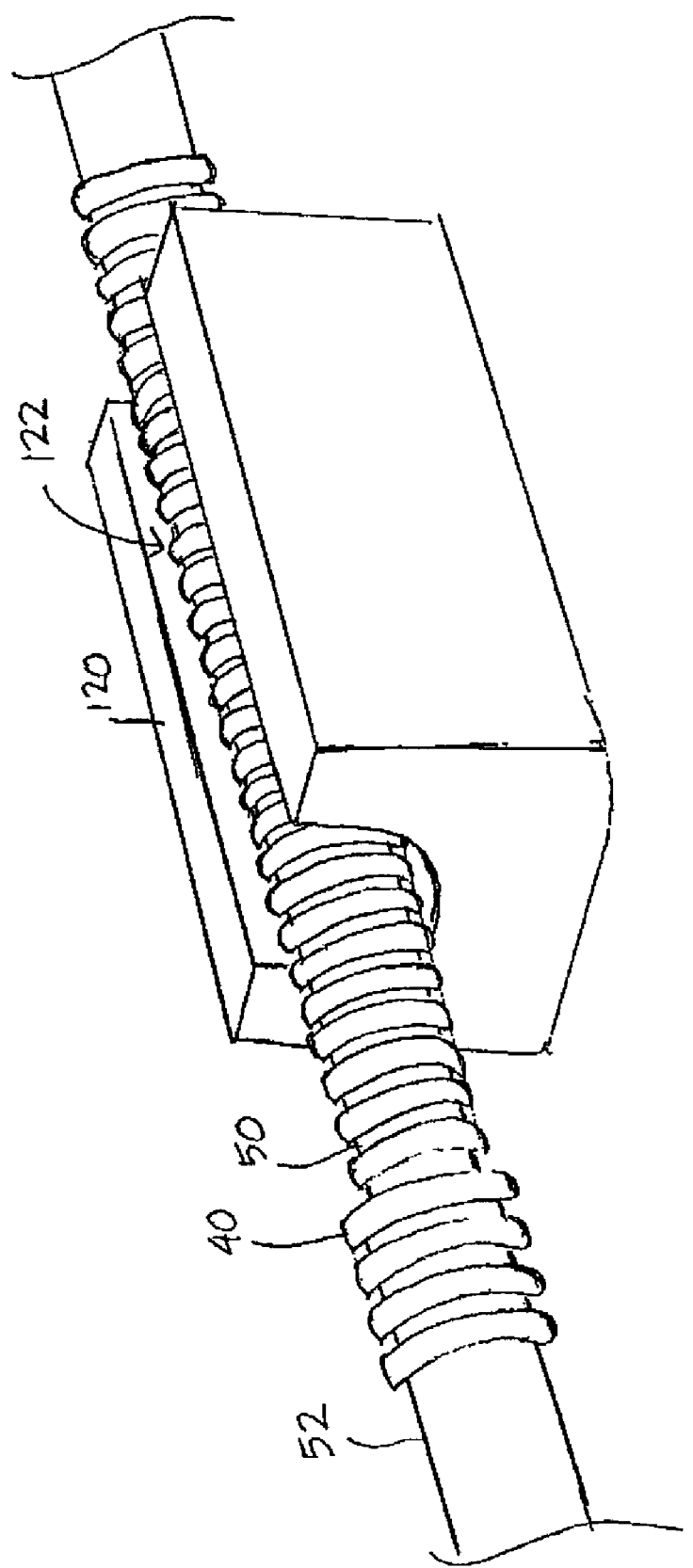

METHODS AND APPARATUS FOR JOINING SMALL DIAMETER CONDUCTORS WITHIN MEDICAL ELECTRICAL LEADS

FIELD OF THE INVENTION

The present invention relates to medical electrical leads and more specifically to a conductor connector assembly and method for joining small diameter conductors to standard sized components.

BACKGROUND OF THE INVENTION

Implantable cardiac leads for sensing cardiac signals or delivering pacing or defibrillation impulses to the heart are typically connected to an implantable or external medical device such as a monitor, pacemaker, or cardioverter defibrillator. Cardiac leads may be for temporary or chronic use and provide an electrical pathway between the heart and an associated device. Electrodes located generally at or near the distal end of a lead are coupled to an associated conductor that extends the length of the lead to a connector assembly at the proximal end of the lead that is connected to the associated device.

Conductors commonly used in cardiac leads include a single wire, a mono- or multi-filar coil, drawn brazed, stranded conductors or cabled conductors. Conductors are typically formed from a single conductive metal or alloy material, such as MP35N alloy, or a composite conductive material, such as a silver core wire clad with MP35N alloy. Conductors may be arranged within multiple lumens of a lead body or arranged concentrically within a common lumen.

Conductors are generally joined to lead components, such as an electrode or connector assembly component, by a mechanical joint to form reliable electrical coupling between the conductor and a component. Welding may not be a practical method for joining conductors to lead components due to dissimilar materials that may be present in the conductor. Therefore, a mechanical joint, such as a crimp or a stake is generally preferred. Lead components are often provided with a conductor bore for receiving a conductor. The outer diameter of the bore may then be crimped or staked to cause the inner diameter to be deformed against the conductor and thereby mechanically retain the conductor within the bore and at the same time provide electrical coupling between the conductor and lead component.

Many considerations are taken into account when optimizing the design of a lead. For example, minimizing lead size is important since a smaller lead body is more readily implanted within the cardiac structures or coronary veins of a patient. It is desirable to minimize the lead body diameter by reducing the diameter of conductors carried by the lead. A reduced diameter conductor must be securely connected, both mechanically and electrically, to an electrode or other lead component to ensure proper lead function. Cardiac leads can undergo considerable stresses due to repetitive flexing caused by the motion of the beating heart and forces applied to the lead during an implantation or repositioning procedure. Mechanical joints must reliably withstand these stresses such that breaks in the electrical pathway between the heart and an implanted device do not occur.

Lead components may be provided in standard sizes. For example, lead connector assemblies are generally manufactured according to industry set standards, such as the IS-1 standard, so that leads are compatible with different types of implantable devices. Therefore, a downsized lead body may be fitted with a relatively larger, standard-sized connector assembly. A conductor bore provided on standard-sized components may be too large to be crimped or staked securely around a small diameter conductor. Depending on the machining methods used, the minimum inner diameter of a conductor bore may be limited resulting in a bore that is too large to be effectively crimped around a small diameter conductor.

What is needed therefore, is a conductor assembly and method for mechanically joining a relatively small diameter conductor to a relatively larger-sized conductor bore provided on an associated lead component, which may be a standard sized component. The conductor assembly and method should provide reliable electrical and mechanical coupling of the conductor to an associated component. Furthermore, the assembly and method should allow standard-sized or modular components to be compatible with non-standard or downsized conductors.

SUMMARY OF THE INVENTION

The present invention addresses the above described needs by providing a conductor assembly and method that includes a sizing member for upsizing the outer diameter of a conductor to fit a relatively larger lead component conductor bore, or, conversely, to downsize a relatively larger conductor bore to receive a relatively smaller diameter conductor. By upsizing the small diameter conductor, or downsizing the large diameter bore, a reliable mechanical joint and electrical coupling may be made between the conductor assembly and lead component.

In a preferred embodiment, a conductor-sizing member is formed from coiled wire that is made from a biocompatible, conductive material. In an alternative embodiment, a sizing member is formed as an elongated collar, which may be generally tubular or C-shaped. The inner diameter of the sizing member is dimensioned to fit securely around the conductor, or the outer diameter of the sizing member is dimensioned to fit securely within the conductor bore. A secure fit may be, for example, an approximately line-to-line fit. The outer diameter of the sizing member is dimensioned such that it may slide easily into a lead component conductor bore and allow an effective crimp, stake or other mechanical joint to be made that mechanically retains the sizing member and the conductor therein and provides electrical coupling between the conductor and lead component. The sizing member may be placed over an exposed end of the conductor before inserting it into the conductor bore, or it may be inserted directly into a lead component conductor bore. The sizing member may be provided with a length sufficient to extend from the conductor bore over a portion of the conductor outside of the bore to thereby provide strain relief to the conductor at a flexion point that exists at the entrance of the conductor bore.

The sizing member and method of use provided by the present invention allows a small diameter conductor to be used with a relatively larger sized conductor bore, groove, slot, sleeve or other feature for receiving a conductor on a lead component, which may be a standard sized or modular lead component. Lead components may be thus be manufactured according to a standard specification and still be used with conductors of different sizes in different lead models by using an appropriately dimensioned conductor sizing sleeve. The sizing member may also be used in splicing two conductors of different sizes together in a splicing sleeve that has a single inner diameter, such that modular lead assemblies that include differently sized conductors may be joined.

BRIEF DESCRIPTION OF THE DRAWINGS

FIG. 1 is a plan view of a cardiac pacing lead representative of one type of medical lead in which the present invention may be used.

FIG. 2 is an end view of a ring electrode component included in the lead of FIG. 1.

FIG. 3 is a side view of a tip electrode component included in the lead of FIG. 1.

FIG. 4 is a perspective view of a preferred embodiment of a conductor-sizing member provided by the present invention.

FIG. 5A is an illustration of a method for assembling the sizing member of FIG. 4 with a conductor and lead component.

FIG. 5B is a section view illustrating the assembly of the sizing member of FIG. 4 with a conductor and lead component.

FIG. 6A illustrates an alternative method of using a sizing member in accordance with the present invention wherein a large diameter conductor is spliced to a small diameter conductor.

FIG. 7 is a perspective view of an alternative embodiment of a conductor-sizing member.

FIG. 8A is an end view of a lead component having a conductor bore wherein the sizing member of FIG. 7 is inserted.

FIG. 9 is a perspective view of an alternate embodiment wherein a conductor assembly includes a sizing member contained in a conductor groove of a lead component.

DETAILED DESCRIPTION OF THE INVENTION

Figure 6B:
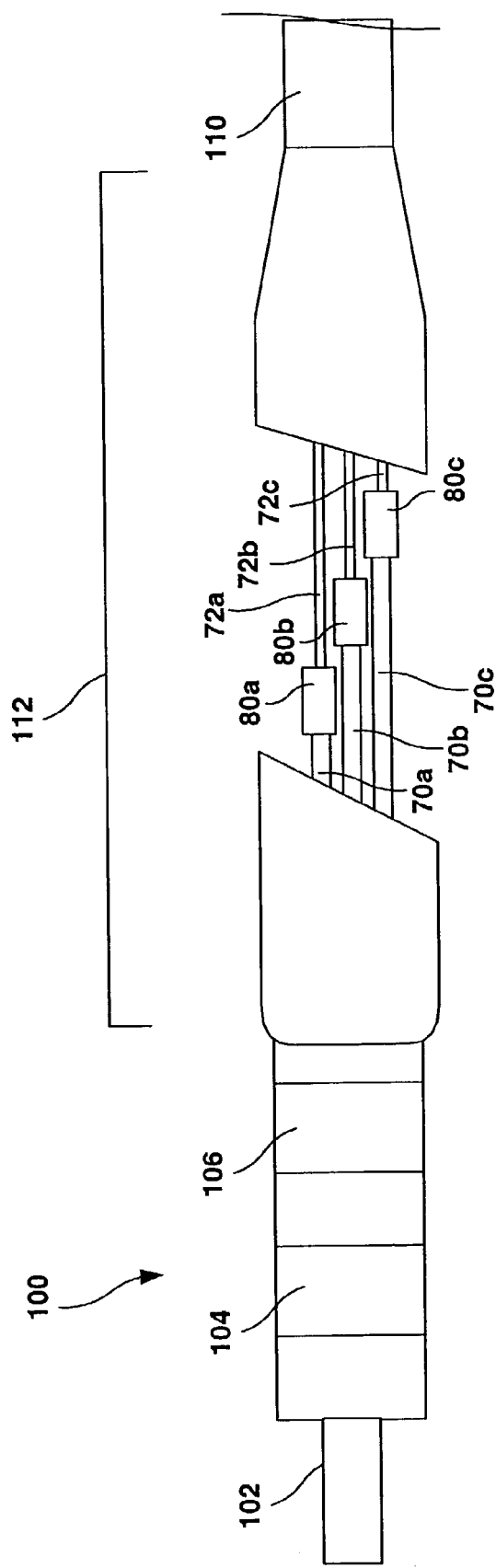
FIG. 6B is a plan view with a cut-away section illustrating a lead assembly incorporating a plurality of large diameter conductors spliced to a plurality of small diameter conductors.

The present invention is directed at providing a method for mechanically joining a small diameter conductor with an associated medical lead 10 component having a relatively larger conductor bore. FIG. 1 is a plan view of a representative cardiac pacing lead 10 representative of one type of medical lead in which the present invention may be used. Numerous cardiac pacing, sensing, or defibrillation leads are known in the art, which may be unipolar, bipolar or multi-polar leads (having one, two, or more electrodes). The present invention may also be implemented in other types of medical leads that may be used for sensing or stimulating excitable tissue in other parts of the body, which may include skeletal muscle, peripheral nerves, the central nervous system, brain tissue, smooth muscle, etc. In addition or in lieu of coupling together parts used for such sensing or stimulating functions, the present invention may be advantageously employed to couple diverse sensors deployed by or coupled to a portion of a medical lead. Such diverse sensors include transducers for measuring or monitoring pressure, temperature, flow, pH and the like as well as sensing the presence or concentration of diverse materials (e.g., glucose, lactate, oxygen or other gases and the like). Accordingly, the lead shown in FIG. 1 is considered exemplary and intended only to illustrate the types of lead components that may be coupled to a conductor using the method included in the present invention, not to limit the use of the invention.

Lead 10 shown in FIG. 1 is a bipolar lead having a tip electrode 14 located at the distal end of lead 10 and a ring electrode 16 spaced proximally from tip electrode 14. Tip electrode 14 and ring electrode 16 are carried by an elongated, flexible lead body 12 that extends to a proximal connector assembly 18. Electrical conductors extend within one or more lumens of lead body 12 between respective electrodes and connectors located on connector assembly 18. The electrodes and connectors are preferably electrically and mechanically coupled according to the present invention as will be described in greater detail hereinbelow. One such conductor extends between tip electrode 14 and connector pin 22. Another conductor extends between ring electrode 16 and connector ring 20. Connector assembly 18 further includes sealing rings 24 which form a fluid tight seal with the inner diameter of a connector port located on an associated medical device to prevent fluid leakage between connector ring 20 and connector pin 22.

FIG. 2 is an end view of ring electrode 16. Ring electrode 16 is formed of a biocompatible, conductive metal, typically a platinum-iridium alloy. Ring electrode 16 includes a conductor bore 28 for receiving a corresponding conductor. The minimum diameter of conductor bore 28 may be limited due to machining methods. A minimum conductor bore diameter may typically be on the order of 0.01 to 0.012 inches. The bore may be crimped or staked at a location approximately indicated by arrow 17, or at a location approximately indicated by arrow 19, or at both locations, to form a mechanical joint with an appropriately sized conductor inserted into bore 28.

FIG. 3 is a side view of tip electrode 14. Tip electrode 14 is shown as a generally hemispherical electrode having a shank 30 having a conductor bore 32 formed therein for receiving an associated conductor. Shank 30 may be crimped at locations approximately indicated by arrows 31 to mechanically join and electrically couple tip electrode 14 with an appropriately sized conductor inserted into bore 32.

Ring electrode 16 and tip electrode 14 are two types of components that may be used in conjunction with the present invention. Other types of components that may be used include connector rings, connecter pins, or other lead components such as a crimp sleeve, for example a crimp sleeve corresponding to that generally disclosed in U.S. Pat. No. 5,676,694 issued to Boser et al., incorporated herein by reference in its entirety, or any other component known for used in medical leads that requires connection to a conductor.

FIG. 4 is a perspective view of a preferred embodiment of a conductor assembly sizing member 40. Sizing member 40 is provided for upsizing the outer diameter of a small diameter conductor by inserting a portion of the conductor (not depicted in FIG. 4) into lumen 42. Alternatively, the same sizing member 40 may be used to downsize a relatively larger diameter conductor bore of a lead component so that a relatively smaller diameter conductor may be joined securely within the conductor bore of the lead component. Sizing member 40 is preferably formed as an electrically conductive, coiled wire, which may be a flat wire, round wire or other elongated, coiled material. The coiled wire is preferably tightly wound to maximize the conductive surface area that comes into contact with a conductor and an associated conductor bore. Sizing member 40 may be formed from the same metal or alloy as a conductor or component with which it may be used or another biocompatible conductive metal. Appropriate materials for forming sizing member 40 include, but are not limited to, MP35N, stainless steel, platinum-iridium alloys and the like. The material selected for forming sizing member 40 should be relatively non-reactive with the associated conductor and component materials to prevent corrosion within the lead.

The inner diameter of sizing member lumen 42 is sized for an approximate line-to-line fit about the outer diameter of an associated conductor. The resulting outer diameter of sizing member 40, once assembled onto conductor is sized for both an easy insertion into a corresponding conductor bore, and a snug fit within conductor bore, for subsequent crimping or staking. Alternatively, an outer diameter of sizing member 40 is sized for an approximate line-to-line fit within a corresponding conductor bore and a resulting inner diameter of sizing member lumen 42 allows for both easy insertion and a snug fit of a corresponding conductor therein. Easy insertion is defined by a gap between an outer diameter and an inner diameter of approximately 0.001" to 0.004" such that subsequent mechanical compression (e.g., crimping, crushing, staking, etc.) tightly couples the parts thereby establishing electrical communication and adequate mechanical joint strength between the conductor and component to prevent conductor and component from uncoupling during use.

The outer diameter of sizing member 40 is sized according to the conductor bore of an associated component such that a secure mechanical joint may be formed by crimping or staking and the like. In one embodiment, a sizing member having an outer diameter of approximately 0.01 inches and an inner diameter of approximately 0.006 inches is formed from coiling approximately 0.002 inch diameter wire. A sizing member of these dimensions is appropriate for use with a conductor bore that is approximately 0.011 to 0.012 inches in diameter and a small diameter conductor that is approximately 0.006 inches in diameter. A conductor assembly using the sizing member of the present invention is typically able to withstand pull (i.e., tension) forces of at least approximately 1 to 3 pounds, and preferably approximately 4 to 6 pounds, before failing. Of course, the means of mechanically coupling the parts is important to the ultimate strength of the union formed thereby; however, the tensile strength of the conductor (or conductors) should also be considered with regard to anticipated tension load on the union.

FIG. 5A is an illustration of a method for assembling the sizing member of FIG. 4 with a conductor and lead component. A conductor 50 is shown as a cable conductor which may generally correspond to a conductor as disclosed in U.S. Pat. No. 5,760,341 issued to Laske et al., or U.S. Pat. No. 5,246,014, issued to Williams et al., and both patents are incorporated herein by reference in their respective entireties. Alternative types of conductors may also be used in conjunction with the present invention such as a straight wire, a filar of a mono- or multi-filar coiled conductor, or a drawn, brazed stranded conductor or any conductor known for use in medical leads.

Conductor 50 may be provided with an outer insulation 52 for electrically isolating conductor 50 from other conductors or components not intended to be electrically coupled to conductor 50. If present, insulation 52 is removed to expose a portion of conductor 50 that will be inserted into a conductor bore 28 of a lead component, shown here as ring electrode 16.

Conductor 50 may be inserted into sizing member 40 as indicated by arrow 60 and then the sizing member and conductor assembly may be inserted into conductor bore 28 as indicated by arrow 62. The sizing member 40 may alternatively be inserted into conductor bore 28 before the conductor 50 is inserted into sizing member 40. Then the assembly is mechanically compressed (e.g., crimped, staked, crushed, etc.) and thus deformed slightly at one or more discrete locations (one such location is indicated by arrow 64) to mechanically engage sizing member 40 and conductor 50 within bore 28. Sizing member 40 may be fully contained within conductor bore 28. Alternatively, sizing member 40 may extend from bore 28 over conductor 50 and thereby act as a strain relief member to prevent conductor 50 from fracturing due to stresses encountered at the entrance of conductor bore 28, as illustrated in FIG. 5B. And, while not presently preferred, the sizing member 40 may be recessed slightly into bore 28.

FIG. 5B is a section view illustrating the assembly of the sizing member of FIG. 4 with a conductor and lead component. Sizing member 40 is provided with a length such that member 40 exits conductor bore 28 to extend over a segment of conductor 50. As illustrated in FIG. 5B, sizing member 40 can be expanded to fit over a portion of outer insulation 52 of conductor 50. Flexion of conductor 50 at the opening of conductor bore 28, indicated by arrows 41, could potentially cause a fracture of conductor 50 over time. By extending sizing member 40 over conductor 50 to provide strain relief (at the locations or regions generally indicated by arrows 41), this risk of fracture may be minimized.

FIG. 6A illustrates an alternative method of using a sizing member in accordance with the present invention wherein a large diameter conductor is spliced to a small diameter conductor. Although not depicted in FIG. 6A, some lead designs may require two differently sized conductors to be used along a conductive pathway. For example, a small diameter lead body may be fitted with a standard sized connector assembly. Because considerable strain can be imposed at the junction of a connector assembly and a lead body, a more robust, larger diameter conductor may be preferred for extending from a connector assembly to the proximal portion of a lead body. However, a small diameter conductor may be preferred for extending the remainder of the lead body to a distal electrode in order to minimize the size of the lead extending through or into portions of a patient's anatomy (e.g., vasculature, cardiac chambers, cardiac tissue, cranium, brain, organs, bones, vessels and the like). In other lead designs, a conductor having certain properties, such as strength, extensibility, etc., may be desired to extend in one direction from a lead component and a conductor having different properties may be desired to extend in the opposite direction from a lead component. The difference in desired properties may result in different conductor sizes along different portions of a common electrical pathway. The present invention provides a method for splicing a larger diameter conductor to a smaller diameter conductor by using a sizing member within a splicing sleeve having a single inner diameter.

A splicing sleeve 80 is shown in FIG. 6A as a generally tubular member, which is preferably formed of a biocompatible conductive material. Splicing sleeve 80 may optionally be provided with an outer insulating coating. Splicing sleeve 80 has an inner lumen 82 sized to receive a larger conductor 70 at first end 81 and be crimped, staked or otherwise mechanically joined with a large diameter conductor 70. Large diameter conductor 70 may be inserted into splicing sleeve 80 at a first end 81 to a desired depth and sleeve 80 may be crimped at locations indicated approximately by arrows 84.

A sizing member 40 may be inserted into splicing sleeve 80 at a second end 83. A small diameter conductor 72 may then be inserted into sizing member 40 and a mechanical joint may be formed between sleeve 80, sizing member 40, and small diameter conductor 72 by crimping at locations indicated approximately by arrows 86. Sizing member 40 may advantageously extend from splicing sleeve 80 over conductor 72 and provide strain relieve to conductor 72 to prevent fracture of conductor 72 due to flexing where it exits sleeve 80 at end 83. Alternatively, sizing member 40 may be provided with a length such that it is fully contained within splicing sleeve 80.

FIG. 6B is a plan view with a cut-away section illustrating a lead assembly incorporating a plurality of large diameter conductors (70*a-c*) spliced to a plurality of small diameter conductors (72*a-c*). In FIG. 6B, a connector assembly 100 having an electrically conductive connector pin 102 and two electrically conductive connector rings 104 and 106 is shown coupled to a small diameter lead body 110 via a junction 112. The connector assembly 100 may be a standard sized connector assembly and is provided with relatively large diameter conductors 70*a-c*, each electrically coupled to a one of the connector pin 102, connector ring 104 and connector ring 106. Lead body 110 is a small diameter lead body carrying relatively small diameter conductors 72*a-c* that must be electrically coupled to larger diameter conductors 70*a-c*. Junction 112 therefore includes splicing sleeves 80*a*, 80*b*, and 80*c* for mechanically joining and electrically coupling small diameter conductors 72*a-c* with large diameter conductors 70*a-c*, respectively, according to the methods generally described in conjunction with FIG. 6A above. Sizing members (not shown in FIG. 6B) are used for downsizing the splicing sleeves 80*a-c* to allow a reliable mechanical joint to be formed with conductors 72*a-c*.

FIG. 7 is a perspective view of an alternative embodiment of a conductor assembly sizing member 44. Sizing member 44 may be formed as an elongated collar member sized to fit around a small diameter conductor. Sizing member 44 may be generally C-shaped on its inner diameter and sized to fit securely the outer diameter of an associated conductor to form good electrical contact with the conductor. Sizing member 44 may be generally C-shaped on its outer diameter or be shaped according to a geometry of a conductor bore on an associated component such that a secure mechanical joint may be formed by crimping or staking.

FIG. 8A is an end view of a lead component having a conductor bore 28 wherein the C-shaped sizing member of FIG. 7 is inserted. The lead component may be ring electrode 16 shown in FIG. 2 having a conductor bore 28 that is relatively large in diameter compared to a small diameter cabled conductor 45. When used in conjunction with a larger diameter conductor (not shown), conductor bore 28 may be crimped or staked at a location approximately indicated by arrow 17, or at a location approximately indicated by arrow 19, or at both locations, such that the conductor is mechanically retained within bore 28. In accordance with the present invention, a C-shaped sizing member 44 is provided to up-size the outer diameter of smaller conductor 45 to allow a secure crimp or stake joint to be formed. The sizing member 44 acts as a shim to fill vacant space within bore 28 thereby effectively mechanically coupling and establishing electrical communication between conductor 45 and component 16.

Figure 8C:
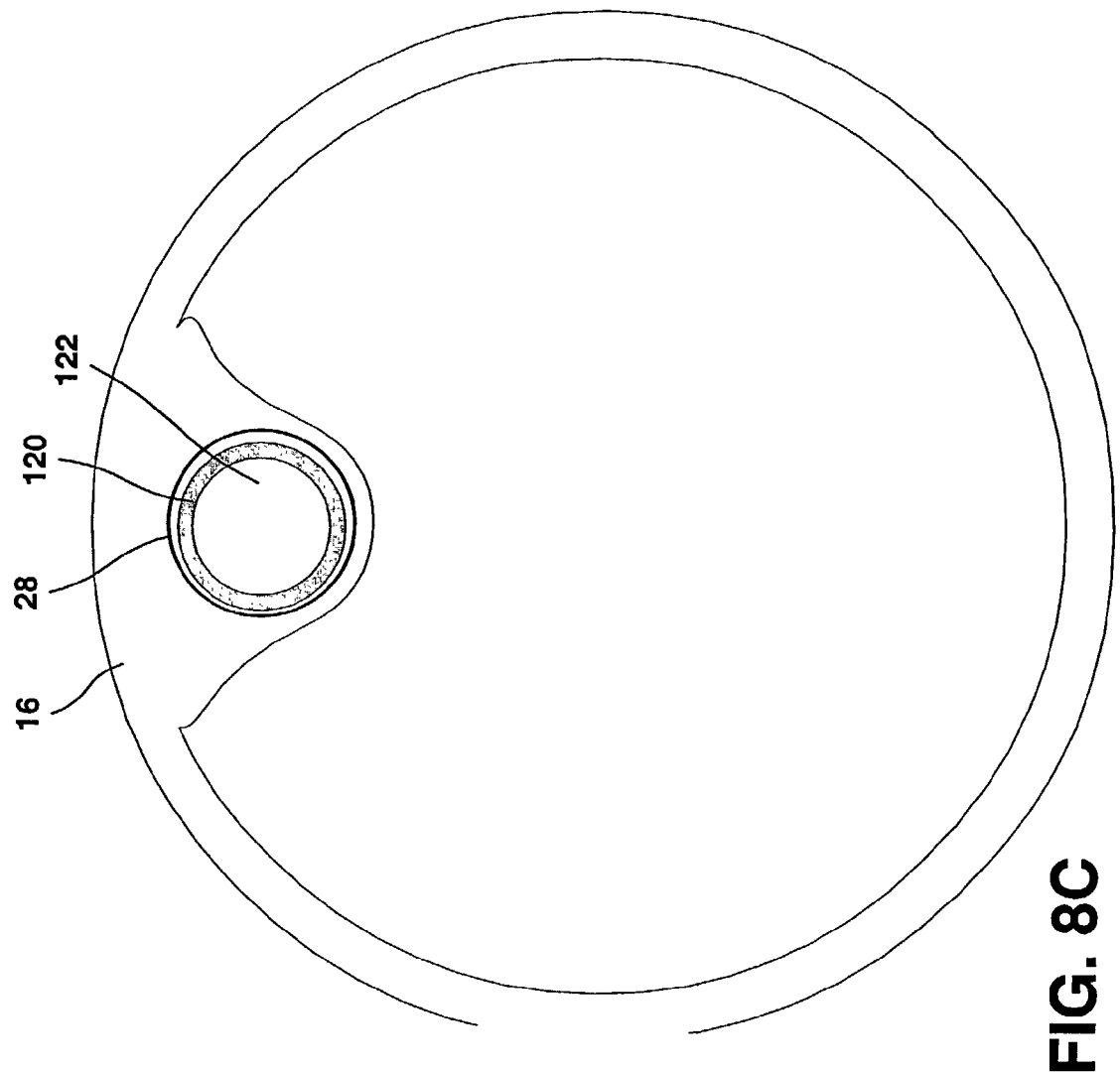
FIG. 8C is an end view illustrating an alternative embodiment of a sizing member that is fit within a conductor bore
Figure 8B:
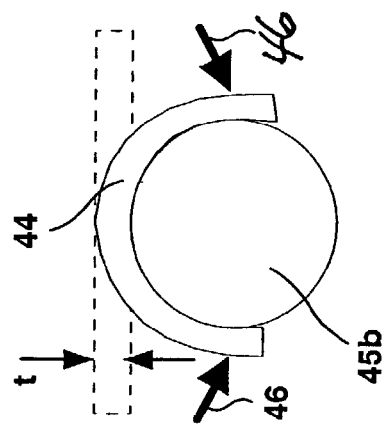
FIG. 8B illustrates a method for forming the sizing member of FIG. 7 about a conductor

FIG. 8B illustrates a method for forming the sizing member of FIG. 7 about a conductor. Sizing member 44 may be provided pre-formed in a general C-shape as shown in FIG. 8A such that it may be inserted over the end of a conductor or into a conductor bore. Alternatively, sizing member 44 may initially be provided as a flat foil sheet. As indicated by dashed lines in FIG. 8*b* the foil sheet appears rectangular but may be of any suitable geometric, irregular or other shape. Sizing member 44 is provided with a thickness (t) indicted by opposing arrows, corresponding to the diameter increase needed to upsize a conductor to fit a lead component conductor bore. Sizing member 44 may be formed around element 45*b*, which may be a small diameter conductor, as indicated by arrows 46 shown in FIG. 8*b*. Sizing member 44 encircles a portion of the circumference of conductor 45 and effectively increases the outer diameter along that portion of the circumference, thereby allowing a reliable mechanical joint to be formed with a conductor bore as previously shown in FIG. 8A.

In an alternative embodiment, an elongated and appropriate size and shape member 45*b* may be used as a mandrel and installation tool used to first shape sizing member 44 and then insert member 44 into a conductor bore to downsize the bore to fit a relatively smaller diameter conductor. The member 45*b* is then retracted from the bore and the conductor inserted into the down-sized conductor bore and sizing member assembly. Then the resulting assembly is mechanically compressed as previously described.

FIG. 8C is an end view illustrating an alternative embodiment of a sizing member fitted within a conductor bore. A generally tubular sizing member 120 is shown inserted into conductor bore 28 of lead component 16. A small diameter conductor (not shown) may be inserted into lumen 122 of sizing member 120. The tubular sizing member 120 may alternatively be inserted over a conductor before inserting member 120 into bore 28.

FIG. 9 is a perspective view of an alternate embodiment of the present invention wherein a conductor assembly includes a sizing member contained in a U-shaped conductor groove of a lead component. A lead component may be formed having a groove, slot, generally C-shaped or generally U-shaped longitudinal opening for receiving a conductor, in contrast to a generally circular, or otherwise enclosed, conductor bore as described the embodiments above. In FIG. 9, a lead component 120 is shown having a generally U-shaped conductor groove 122, which may be crimped, staked or otherwise mechanically joined to a conductor extending therethrough. Sizing member 40, which corresponds to the sizing member shown previously in FIG. 4, is assembled over small diameter conductor 50 and positioned in conductor groove 122. Sizing member 40 is provided with a length greater than groove 122 such that member 40 extends over conductor 50, and may extend over conductor insulation 52, to provide strain relief to conductor 50 as described previously.

Thus a conductor assembly and method has been described that includes a conductor sizing member for upsizing a small diameter conductor to thereby allow a mechanical joint to be formed between the conductor and a larger diameter conductor bore located on a lead component. The present invention thus allows relatively small diameter conductors to be used in conjunction with standard sized lead components or modular lead assemblies or components. Aspects of the present invention may be used in numerous types of medical leads with numerous types of components that need to be electrically coupled to a conductor.

While coiled conductive wire and sheets of conductive foil have been described with respect to most illustrated embodiments, the present invention is not limited to such illustrated embodiments. For example, the wire may have a common diameter and be fabricated in either a coil having a common diameter or as a helical coiled member. Conversely, the wire may have a different diameter from a first end to a second end so that when coiled, it has a gradual increasing or decreasing longitudinal cross section. If desired, the material comprising the sizing member 40 may also be rendered with smooth exterior and/or interior surfaces or may have a textured, or roughened surface, and the like. In addition, in lieu of a single coiled member the sizing member may comprise more than one wire braided or woven into a mesh or scrim. In such an embodiment wherein the sizing member is a tubular mesh unit the diameter of the unit may increase under longitudinal compression and decrease under longitudinal tension.

Specific descriptions of cardiac leads and cardiac lead components provided herein, therefore, are intended to illustrate the concepts of the invention and are not intended to be limiting with regard to the following claims.

The invention claimed is:

1. A medical electrical lead, comprising:
   an elongated flexible conductor including an insulated portion having an outer insulation, and an un-insulated portion extending longitudinally from the insulated portion;
   a lead component including a sidewall extending about the un-insulated portion of the conductor;
   a mechanical and electrical coupling formed between the lead component and the un-insulated portion of the conductor, the coupling contained within the lead and formed by a mechanical compression of the lead component sidewall toward the un-installed portion of the conductor; and
   an un-insulated electrically conductive coiled wire disposed about the conductor, the coil wire including a first portion extending between the un-insulated portion of the conductor and the lead component sidewall at the coupling, and a second portion extending over the conductor, beyond both the coupling and the component to provide strain relief for the conductor beyond the component within the lead.

2. A medial electrical lead according to claim 1, wherein the lead component comprises an electrode.

3. A medical electrical lead according to claim 1, wherein the sidewall of the lead component extended partially about the un-insulated portion of the conductor before the coupling was formed.

4. A medical electrical lead according to claim 1, wherein the sidewall of the lead component extended completely about the un-insulated portion of the conductor before the coupling was formed.

5. A medical eletrical lead according to claim 4, wherein:
   the un-insulated portion of the conductor was formed having a diameter of approximately 0.006 inch;
   the coiled wire was formed having an inner diameter of approximately 0.006 inch. and an outer diameter of approximately 0.01 inch, the inner diameter receiving the conductor therein before the coupling was formed; and
   the bore was formed having a diameter between approximately 0.011 inch and 0.012 inch, to receive the coil therein before the coupling was formed.

6. A medical electrical lead according to claim 1, wherein the coiled wire has been tightly wound.

7. A medical electrical lead according to claim 1, where in the component sidewall was formed such that a gap existed between the sidewall and the first portion of coiled wire before the coupling was formed, the gap being between approximately 0.001 inch and 0.004 inch.

8. A medical electrical lead according to claim 1, wherein the coiled wire was formed such that a gap existed between the first portion of the coiled wire and the un-insulated portion of the conductor before the coupling was formed, that gap being between approximately 0.001 inch and 0.004 inch.

9. A medical electrical lead according to claim 1, wherein the component sidewall was formed such that a line-to-line fit existed between the sidewall and the first portion of the coiled wire before the coupling was formed.

10. A medical electrical lead according to claim 1, wherein the coiled wire was formed such that a line-to-line fit existed between the first portion of the coiled wire and the un-insulated portion of the conductor before the coupling was formed.

11. A medical electrical lead according to claim 1, wherein the second portion of the coiled wire further extends over the outer insulation of the conductor.

* * * * *